(12) United States Patent
Pora et al.

(10) Patent No.: US 9,476,074 B2
(45) Date of Patent: *Oct. 25, 2016

(54) STRAIN OF MICROALGA THAT PRODUCES SQUALENE

(75) Inventors: Bernard Pora, Wuhan (CN); Jie Zhou, Wuhan (CN); Sophie Defretin, Bethune (FR); Xavier Vandewalle, Steenvoorde (FR)

(73) Assignee: ROQUETTE FRERES, Lestrem (FR)

( * ) Notice: Subject to any disclaimer, the term of this patent is extended or adjusted under 35 U.S.C. 154(b) by 184 days.

This patent is subject to a terminal disclaimer.

(21) Appl. No.: 14/118,605

(22) PCT Filed: May 18, 2012

(86) PCT No.: PCT/EP2012/059231
§ 371 (c)(1),
(2), (4) Date: Nov. 19, 2013

(87) PCT Pub. No.: WO2012/159980
PCT Pub. Date: Nov. 29, 2012

(65) Prior Publication Data
US 2014/0113015 A1    Apr. 24, 2014

(30) Foreign Application Priority Data
May 20, 2011 (CN) .......................... 2011 1 0147066

(51) Int. Cl.
| | |
|---|---|
| C12P 5/02 | (2006.01) |
| C12P 7/64 | (2006.01) |
| A23L 1/03 | (2006.01) |
| A23L 1/30 | (2006.01) |
| A61K 31/01 | (2006.01) |
| A61K 31/202 | (2006.01) |
| C12P 5/00 | (2006.01) |
| C12R 1/89 | (2006.01) |

(52) U.S. Cl.
CPC ............ *C12P 7/6427* (2013.01); *A23L 1/0345* (2013.01); *A23L 1/3006* (2013.01); *A23L 1/3014* (2013.01); *A61K 31/01* (2013.01); *A61K 31/202* (2013.01); *C12P 5/007* (2013.01); *C12P 5/026* (2013.01); *C12R 1/89* (2013.01)

(58) Field of Classification Search
None
See application file for complete search history.

(56) References Cited

U.S. PATENT DOCUMENTS

| | | |
|---|---|---|
| 5,130,242 A * | 7/1992 | Barclay .................. A23K 1/008 426/49 |
| 6,248,779 B1 | 6/2001 | Shimizu et al. |
| 2014/0073037 A1 | 3/2014 | Patinier |
| 2014/0088201 A1 | 3/2014 | Pora et al. |
| 2015/0140030 A1 | 5/2015 | Looten et al. |
| 2015/0159116 A1 | 6/2015 | Patinier et al. |

FOREIGN PATENT DOCUMENTS

| | | |
|---|---|---|
| EP | 2 650 356 | 10/2013 |
| WO | WO 2007/039149 | 4/2007 |
| WO | WO 2010/023551 | 3/2010 |
| WO | WO 2012/077799 | 6/2012 |
| WO | WO 2012/159979 | 11/2012 |
| WO | WO 2012/164211 | 12/2012 |
| WO | WO 2013/156720 | 10/2013 |
| WO | WO 2013/178936 | 12/2013 |

OTHER PUBLICATIONS

Yokoyama et al., Mycoscience (2007) 48:199-211.*
Nakazawa, A. et al. "Optimization of culture conditions of thraustochytrid,*Aurantiochytrium* sp. strain 18W-13a for squalene production" *The 1st Asia Oceania Algae Innovation Summit*, Dec. 13, 2010, pp. 1-2.
Tsui, C. et al. "Labyrinthulomycetes phylogeny and its implications for the evolutionary loss of chloroplasts and gain of ectoplasmic gliding" *Molecular Phylogenetics and Evolution*, Jan. 1, 2009, pp. 129-140, vol. 50, No. 1.
Database GenBank [Online] Accession No. DQ367050.1, "*Schizochytrium* sp. ATCC 20888 18S ribosomal RNA, partial sequence" Sep. 30, 2006, pp. 1-2, XP-002681840.
Qian, L. et al. "Screening and Characterization of Squalene-Producing Thraustochytrids from Hong Kong Mangroves" *Journal of Agricultural and Food Chemistry*, May 10, 2009, pp. 4267-4272, vol. 57, No. 10.
Jiang, Y. et al. "Fatty Acid Composition and Squalene Content of the Marine Microalga *Schizochytrium mangrovei*" *Journal of Agricultural and Food Chemistry*, Mar. 10, 2004, pp. 1196-1200, vol. 52, No. 5.
Kaya, K. et al. "Thraustochytrid *Aurantiochytrium* sp. 18W-13a Accummulates High Amounts of Squalene" *Bioscience Biotechnology Biochemistry*, 2011, pp. 2246-2248, vol. 75, No. 11.
Nakazawa, A. et al. "Optimization of culture conditions of thraustochytrid, *Aurantiochytrium* sp. strain 18W-13a for squalene production" *Bioresource Technology*, Apr. 1, 2012, pp. 287-291, vol. 109.
Written Opinion in International Application No. PCT/EP2012/059231, Sep. 4, 2012, pp. 1-8.
Chen, G. et al. "Optimization of nitrogen source for enhanced production of squalene from thraustochytrid *Aurantiochytrium* sp" *New Biotechnology*, Sep. 30, 2010, pp. 382-389, vol. 27, No. 4.
Fan, K. et al. "Enhanced production of squalene in the thraustochytrid *Aurantiochytrium mangrovei* by medium optimization and treatment with terbinafine" *World Journal of Microbiology and Biotechnology*, Jan. 8, 2010, pp. 1303-1309, vol. 26, No. 7.
Yue, C.-J. et al. "Impact of methyl jasmonate on squalene biosynthesis in microalga *Schizochytrium mangrovei*" *Process Biochemistry*, Aug. 1, 2009, pp. 923-927, vol. 44, No. 8.
Written Opinion in International Application No. PCT/EP2012/059230, Jul. 10, 2012, pp. 1-9.
Hayashi, M. et al. "Effect of Vitamin B12-Enriched Traustochytrids on the Population Growth of Rotifers" *Biosci Biotechnol. Biochem.*, 2007, pp. 222-225, vol. 71, No. 1.
Currently pending claims of U.S. Appl. No. 14/118,641, 2016, pp. 1-3.
Currently pending claims of U.S. Appl. No. 14/118,674, 2015, pp. 1-2.
Currently pending claims of U.S. Appl. No. 14/394,813, 2015, pp. 1-3.
Allowed claims of U.S. Appl. No. 14/403,611, 2015, pp. 1-2.

* cited by examiner

*Primary Examiner* — Irene Marx
(74) *Attorney, Agent, or Firm* — Saliwanchik, Lloyd & Eisenschenk

(57) ABSTRACT

The invention relates to a novel strain of *Schizochytrium* sp. that can produce large quantities of squalene, the methods for the production of lipid compounds of interest using said strain and the products and compositions prepared with said strain.

2 Claims, No Drawings

STRAIN OF MICROALGA THAT PRODUCES SQUALENE

CROSS-REFERENCE TO RELATED APPLICATION

This application is the U.S. national stage application of International Patent Application No. PCT/EP2012/059231, filed May 18, 2012.

The Sequence Listing for this application is labeled "Seq-List-replace.txt" which was created on Dec. 14, 2013 and is 2 KB. The entire contents of the sequence listing is incorporated herein by reference in its entirety.

The present invention relates to a novel strain of microalgae which is particularly suitable for the production of squalene and to the uses thereof.

Squalene is a triterpene, an isoprenoid comprising 30 carbon atoms and 50 hydrogen atoms, of the formula: 2,6,10,15,19,23-hexamethyl-2,6,10,14,18,22-tetracosa-hexene.

It is a lipid that is naturally produced by all higher organisms, including human beings (found in sebum). Squalene is in fact an essential intermediate in the biosynthesis of cholesterol, steroid hormones and vitamin D (an enzyme of the cholesterol metabolic pathways, squalene monooxygenase, will, by oxidizing one of the ends of the squalene molecule, induce cyclization thereof and result in lanosterol, which will be converted to cholesterol and to other steroids).

Industrially, squalene is especially used in the food sector, the cosmetics field and the pharmaceutical field.

As a food supplement, squalene is usually formulated as capsules or as oils.

In the cosmetics field, this molecule can be used as an antioxidant, an antistatic and an emollient in moisturizing creams, penetrating the skin rapidly without leaving fatty traces or sensations, and mixing well with other oils and vitamins.

In this field, it should be noted that, given the very high instability of squalene (6 unsaturations), it is the saturated form squalane (obtained by hydrogenation), a better antioxidant than squalene, which is found on the market, generally with a very high level of purity (99%).

Toxicological studies have shown that, at the concentrations used in cosmetics, squalene and squalane do not exhibit any toxicity, and are not irritant or sensitizing to human skin.

In the pharmaceutical field, squalene is used as adjuvants for vaccines.

These adjuvants are substances which stimulate the immune system and increase the response to the vaccine.

Squalene has been used, in the form of an emulsion added to the vaccinating substances, in order to make the vaccine more immunogenic, since 1997 in an influenza vaccine (Fluad, from the company Chiron, against seasonal influenza) at approximately 10 mg of squalene per dose.

Like all vaccines containing squalene, these emulsions have a milky white appearance.

Squalene is also used as a vaccine adjuvant, in particular in experimental vaccines, antimalarial substances or influenza vaccine targeting the emerging viruses H5N1, and then in 2009 H1N1, as:
- a patented constituent of the AS03 adjuvant system used by GlaxoSmithKline in the Pandemrix and Arepanrix vaccine against the 2009 influenza pandemic, and
- a patented constituent of the MF59 adjuvant system used by Novartis.

Squalene has also been added to influenza vaccines to stimulate the immune response of the human body through the production of memory CD4 cells.

It is the first oil-in-water adjuvant for influenza vaccines to have been marketed in combination with the seasonal influenza virus antigens.

The level of purity of the squalene is essential in this application field.

Indeed, if it is taken orally, squalene is considered to be completely safe; however, the injectable route is the subject of controversy.

Indeed, in the medical field, the risk of harm for a human recipient may be increased in situations where squalene is contaminated with impurities, since, by definition, this adjuvant can also induce a strong immune response against its own impurities.

It is therefore essential to have high-quality squalene free of impurities (traces of metals, in particular of mercury, and of other toxins).

A certain number of pathways for producing squalene are proposed in the literature.

It is a compound which is often found stored in the livers of cartilaginous fish such as deep-sea sharks (hence its name).

It is therefore one of the reasons why they are overfished, the sharks already being hunted for their fins. Shark livers are now sold to produce gel capsules described as "good for the health".

However, while the squalene marketed is thus mainly extracted from shark livers, it is not free of health problems.

This is because sharks can be infected with pathogens that can produce substances harmful to human beings. In addition, the shark liver, which is the organism's elimination and purification organ, may contain toxins such as carchatoxin which is harmful to human beings.

These environmental concerns (large decrease in shark numbers) and health concerns (fish livers also store toxins that are of concern with regard to health) have prompted its extraction from plants.

It is thus possible to isolate it from olive oil, palm oil, and other oils from cereals or originating from amaranth, seeds, rice bran or wheat germ.

However, the major drawback in this case is that the squalene is extracted in very small amounts, of about from 0.1% to 0.7% by weight.

As a first alternative to these processes of extraction from shark livers or from plants, often made expensive by the implementation of substantial enrichment and purification processes, the first processes for producing squalene from microorganisms—natural yeasts or recombinant yeasts, in particular the *Saccharomyces* type—have been proposed.

Thus, *Saccharomyces cerevisiae* is known for its ability to produce squalene, however in very small amounts: of about 0.041 mg/g of biomass (Bhattacharjee, P. et al., 2001, in *World J. Microb. Biotechnol.*, 17, pp. 811-816).

Work has therefore been carried out on the optimization of these production capacities, by means of genetic recombination.

The recombinant yeasts which produce squalene thus have the advantages:
- of benefitting from the same GRAS (Generally Regarded As Safe) status as the host cell,
- of being free of pathogens, prions or toxins, just like the host cell, and
- of having already been used in the vaccine field (such as those yeasts which express vectors containing hepatitis B antigens).

However, as presented by patent application WO 2010/023551 for the medical field (production of squalene with a purity greater than 97% as a vaccine adjuvant), this first alternative is industrializable only if it is possible to have recombinant yeasts hyperproducing squalene (at more than 15% by weight of dry cells).

As it happens, obtaining these recombinant cells requires the implementation of numerous laborious, lengthy and complex metabolic engineering steps, using molecular biology tools, resulting in the stimulation of the squalene biosynthesis pathways and in the inhibition of the squalene catabolism pathways.

Indeed, as WO 2010/023551 states, there are many genes involved in squalene biosynthesis, including mevalonate kinase, phosphomevalonate kinase, pyrophosphomevalonate decarboxylase, isopentenyl pyrophosphate isomerase, HMGR (3-hydroxy-3-methylglutaryl-CoA reductase) and squalene synthetase.

For the catabolism pathways, genes encode numerous enzymes involved in the conversion of squalene to ergosterol, including squalene epoxidase (ERG1), lanosterol synthetase, C14-dimethylase, d14-reductase, C4-methyloxidase, C4-decarboxylase (ERG26), 3-ketoreductase, C24-methyltransferase, C8-isomerase, C5-desaturase, d22-desaturase and d24-reductase.

Moreover, other catabolic enzymes must also be taken into consideration: LEU2 ([beta]-isopropyl malate dehydrogenase), oxidosqualene cyclase, zymosterol-24-methyltransferase and ergosta-5,7,24(28)-trienol-22-dehydrogenase.

As a second alternative to the processes of extraction from shark livers or from plants, promising processes for producing squalene from microalgae of the Thraustochytriales family (comprising the genera *Thraustochytrium, Aurantiochytrium* and *Schizochytrium*), more particularly *Schizochytrium mangrovei* or *Schizochytrium limacinum*, have been proposed.

These microalgae produce squalene under heterotrophic conditions (absence of light; provision of glucose as a carbon source), and can therefore be easily manipulated by those skilled in the art in the field of microorganism fermentation.

These processes therefore offer, by means of controlled fermentation conditions, qualities of squalene of which the purification can be easily carried out to meet food, cosmetic and medical needs.

In these microalgae of the Thraustochytriales family, squalene is, however, the coproduct of other lipid compounds of interest, such as docosahexaenoic acid (or DHA), a polyunsaturated fatty acid of the ω3 family.

It thus appears that squalene is specially described as one of the components of the unsaponifiable fraction of commercial DHA oils (along with carotenoids and sterols).

By way of comparison, the *Schizochytrium mangrovei* FB1 strain produces DHA in a proportion of 6.2% by dry weight of cells, for 0.017% of squalene.

As a result, these microorganisms which naturally produce squalene do so in small amounts:
  of about 0.1 mg/g of biomass, for Thraustochytrid ACEM 6063 (cf. Lewis et al., in *Mar. Biotechnol.*, 2001, 439-447),
  of about 0.162 mg/g of biomass, for *Schizochytrium mangrovei* FB1 (cf. Jiang et al., in *J. Agric. Food Chem.*, 2004, 52, pp. 1196-1200), and
  of about 0.18 mg/g of biomass, for an isolate from Hong Kong mangrove *Aurantiochytrium* BR-MP4-A1 (cf. Li et al, in *J. Agric. Food Chem.*, 2009, 57, pp. 4267-4272).

In order to increase production, it therefore appeared to be essential to optimize the fermentation conditions.

In the article by Qian Li et al., in *J. Agric. Food Chem.*, 2009, 57, 4267-4272, it is specified that squalene is a key intermediate of sterol biosynthesis, and that the first step of the conversion of squalene to sterols is catalyzation by an oxygen-dependent squalene epoxidase.

Conditions rich in dissolved oxygen are therefore to be prohibited if it is desired, on the contrary, to accumulate intracellular squalene.

Thus, culturing Thraustochytrid ACEM 6063 at a low dissolved oxygen level (0 to 5% saturation) makes it possible to accumulate more than 1 mg/g of squalene, whereas growth at a higher dissolved oxygen level (40% to 60%) makes it possible to achieve only 0.01 mg/g of squalene.

Likewise, culturing at a temperature of 15° C. puts the production of squalene by Thraustochytrid ACEM 6063 at 1.2 mg/g, whereas it is only 0.7 mg/g at 20° C. (cf. Lewis et al., in Mar. Biotechnol., 2001, 3, 439-447).

In the article by G. Chen et al., in *New Biotechnology*, 2010, 27-4, pp. 382-389, it is stated that *Schizochytrium* mainly produces DHA, by means of the polyketide synthase (PKS) pathway, whereas squalene is instead synthesized by means of the cholesterol biosynthesis pathway, which means that the nutritional needs of thraustochytrids for these two compounds are distinct.

The object of their work was therefore to systematically investigate the effect of various sources of nitrogen in the production of squalene.

G. Chen et al. thus found that *Schizochytrium* could grow rapidly and accumulate "high" amounts of squalene in a culture medium containing a mixture of nitrogenous sources consisting of monosodium glutamate, yeast extract and tryptone.

Despite that, this "high" production of squalene is entirely relative.

If, while the authors succeed in significantly increasing the squalene content and the yield by 26.3% and 10.1%, respectively, relative to the values of the basic medium, these optimized conditions in fact produce a squalene content of 0.72 mg/g and a titer of 5.90 mgl/l.

With this same objective of optimizing squalene production, K. W. Fan et al., in World J. Microbiol. Biotechnol., 2010, 26-3, pp. 1303-1309, used an inhibitor of squalene monooxygenase (a key enzyme in sterol biosynthesis): terbinafine hydroxychloride.

It is known that the squalene content and yield are linked to the age of a microorganism culture.

The more the cell culture ages, the less it accumulates squalene; in fact, the more it consumes said squalene in the sterol biosynthesis pathway.

Terbinafine therefore acts by preventing this consumption of squalene toward the sterol pathway and therefore makes it possible to stimulate the intracellular accumulation of squalene by up to 36% to 40% relative to the control.

However, the highest squalene production obtained with the *Aurantiochytrium mangrovei* FB3 strain used in this study, even though much higher than that described for *S. cerevisiae* (0.041 mg/g of biomass), or even that described for *Torulaspora debrueckii* (0.24 mg/g of biomass), is only 0.53 mg/g of biomass.

Thus, despite all the efforts made, these values are much lower than the reference values for olive oil (of about 4.24 mg/g) and are far from the values required on the industrial scale.

Concerned with developing a process of production which is much more effective and much less expensive than those described in the prior art, the applicant company has, during its research, identified a new strain of microalgae having an exceptional capacity for squalene production, since it allows a production of more than 10 mg of squalene per g of biomass, for example 18 mg of squalene per g of biomass, i.e., 30 times more than the highest squalene production obtained with the *Aurantiochytrium mangrovei* FB3 strain. Moreover, in addition to its remarkable squalene production capacity, this strain also makes it possible to obtain other lipid compounds of interest, such as docosahexaenoic acid (DHA), at more than 15% by dry weight of biomass, for example 17.6% by dry weight of biomass.

This *Schizochytrium* sp. strain was deposited in France on Apr. 14, 2011, with the Collection Nationale de Cultures de Microorganismes [National Collection of Microorganism Cultures] of the Institut Pasteur (CNCM) under number 1-4469, and also in China with the CHINA CENTER FOR TYPE CULTURE COLLECTION (CCTCC) of the University of Wuhan, Wuhan 430072, P.R. China, under number M 209118. It was characterized by partial sequencing of the gene encoding the 18S RNA (SEQ ID No 1):

```
  1 GAGGGTTTTA CATTGCTCTC aTTCCaATAG CAaGACGCGA AGCGCCCCGC ATTGATATTT

61 CTCGTCACTA CCTCGTGGAG TCCACATTGG GTAATTTACG CGCCTGCTGC CTTCCTTGGA

121 TGTGGTAGCC GTCTCTCAGG CTCCCTCTCC GGAGTCGAGC CCTAACTCCC CGTCACCCGT

181 TATAGTCACC GTAGGCCAAT ACCCTACCGT CGACAACTGA TGGGGCAGAA ACTCAAACGA

241 TTCATCGCTC CGAAAAGCGA TCTGCTCAAT TATCATGACT CACCAAGAGA GTTGGCTTAG

301 ACCTAATAAG TGCGGCCCTC CCCGAAAGTC GGGCCCGTAC AGCACGTATT AATTCCAGAA

361 TTACTGCAGG TATCCGTATA AAGGAACTAC CGAAGGGATT ATAACTGATA TAATGAGCCG

421 TTCGCAGTTT CACAGTATAA TTCGCTTATA CTTACACATG CATGGCTTAG TCTTTGAGA
``` which made it possible to identify it as being a strain of the *Schizochytrium* sp. type.

Consequently, the present invention relates to the *Schizochytrium* sp. strain deposited on Apr. 14, 2011, with the CNCM under number 1-4469. This strain may be subsequently denoted "CNCM 1-4469" in the present application.

This strain has the advantageous property of producing squalene in large amounts. Indeed, it makes it possible to obtain squalene on a scale of 1 gram for 100 grams of dry biomass. In particular, the quantification of squalene produced can be carried out according to the method detailed in the experimental section.

Consequently, the present invention also relates to a variant of this strain or a strain derived from said strain, said variant or said derived strain retaining the property of producing squalene contents greater than or equal to 1 g per 100 g of dry biomass. In particular, it relates to a *Schizochytrium* sp. strain capable of producing squalene contents greater than or equal to 1 g per 100 g of dry biomass, and obtained from the CNCM I-4469 strain by mutagenesis or by gene transformation. The mutagenesis may be site-directed and/or random.

The present invention also relates to a method for preparing such a strain, comprising mutagenesis or gene transformation of the CNCM I-4469 strain and, optionally, a screening step for selecting the strains producing at least 1 g of squalene per 100 g of dry biomass.

The invention relates to a method for culturing the CNCM I-4469 strain or a variant thereof which retains its squalene production capacity, comprising a step of culturing this strain in an appropriate medium and a step of recovering the biomass. The culturing is carried out under heterotrophic conditions. Generally, the culturing step comprises a pre-culturing step, in order to revive the strain, and then a step of actual culturing or fermentation. The latter step corresponds to the step of producing the lipid compounds of interest.

The conditions for culturing these microalgae are well known in the field. For example, the article by G. Chen mentioned above describes a process comprising the following successive steps:

start from the strain maintained on agar nutritive medium comprising glucose, monosodium glutamate, yeast extract and various trace elements, prepare a preculture in Erlenmeyer flasks on an orbital shaker, at a pH of 6, at a temperature of 25° C. in order to obtain a revived biomass, and inoculate another series of production Erlenmeyer flasks with the same culture medium as that used in the preculture, with about 0.5% (v/v) of the biomass obtained in the previous step, and maintain the temperature at 25° C.

The preculturing may preferably last for 24 to 74 hours, preferably about 48 hours. With regard to culturing, it may preferably last for 60 to 150 hours.

The carbon source required for the growth of the microalgae is preferentially glucose.

With regard to the nature of the nitrogen source, the applicant company has found that it is possible to select it from the group consisting of yeast extracts, urea, sodium glutamate and ammonium sulfate, taken alone or in combination. Likewise, it is possible to totally or partially replace the urea with sodium glutamate, or to use a mixture of sodium glutamate and ammonium sulfate.

It is possible to prefer to the yeast extracts conventionally used in the prior art processes, urea supplemented with a vitamin cocktail, such as the BME cocktail sold by Sigma, used in a proportion of 5 ml/l.

The preculture media preferably comprise vitamins B1, B6 and B12.

With regard to the pH of the culture medium, as will be exemplified hereinafter, it will be maintained between 5.5 and 6.5, preferentially fixed at a value of 6. The pH can be regulated by any means known to those skilled in the art, for example by adding 2 N sulfuric acid, and then with 8 N sodium hydroxide.

Finally, the dissolved oxygen content can be regulated at a value between 20% and 0%, preferably maintained at 5% for an initial period of 24 to 48 hours, preferably 36 hours, before being left at 0%. With regard to the oxygen transfer, it will be regulated by any means known, moreover, to those skilled in the art, so as not to exceed 45 mmol/l/hour.

The invention relates quite particularly to the use of the CNCM I-4469 strain or a variant thereof which retains its squalene production capacity for producing lipid compounds of interest. The lipid compounds of interest comprise squalene and in particular docosahexaenoic acid (or DHA). Preferably, the compound of interest is squalene. It should be noted that the squalene can be produced with contents greater than or equal to 1 g per 100 g of dry biomass.

The invention relates to a method for producing lipid compounds of interest, which comprises culturing the CNCM I-4469 strain or a variant thereof which retains its squalene production capacity, and recovering the biomass rich in lipid compounds of interest and, optionally, harvesting and/or purifying the lipid compounds of interest. The lipid compounds of interest comprise squalene and in particular docosahexaenoic acid (DHA). Preferably, the compound of interest is squalene. In particular, the squalene can be produced with contents greater than or equal to 1 g per 100 g of dry biomass.

After the fermentation step, the biomass is recovered from the fermentation medium by any method known to those skilled in the art; for example the biomass can be removed from the fermenter and simply concentrated by microfiltration or centrifugation, or washed via a succession of concentrations and dilutions with an aqueous solution.

The invention thus relates to the biomass comprising the CNCM I-4469 strain or a variant thereof which retains its squalene production capacity. Quite particularly, after the fermentation or culturing step, this biomass is rich in lipid compounds of interest such as squalene and docosahexaenoic acid, preferably squalene. It can be obtained by means of the method described in the present document. Indeed, after fermentation, the biomass may contain 17.6% by weight of docosahexaenoic acid and 1.8% by weight of squalene. The term "rich in squalene" is intended to mean here a content greater than or equal to 1 g per 100 g of dry biomass.

In addition to the biomass, the present invention also relates to a cell extract or lysate prepared from this biomass comprising the CNCM I-4469 strain or a variant thereof which retains its squalene production capacity. In particular, this extract or lysate is prepared from the biomass recovered after fermentation. This extract or lysate is rich in lipid compounds of interest such as squalene and docosahexaenoic acid, preferably squalene. The rupturing of the cells in order to extract the lipid content can be carried out via various routes, among which are mechanical, chemical or enzymatic routes.

The oil may subsequently be extracted from the cell lysate with hexane/ethanol in several successive extractions. The hexane fraction is subsequently separated and then the hexane is evaporated off so as to isolate the crude oil.

Thus, the method for producing lipid compounds of interest, preferably squalene, comprises harvesting the biomass, preparing a cell extract or lysate and extracting a crude oil comprising the lipid compounds of interest, preferably squalene.

The present invention also relates to a crude or refined oil comprising the lipid compounds of interest, preferably squalene, prepared from this biomass comprising the CNCM I-4469 strain or a variant thereof which retains its squalene production capacity.

The present invention finally relates to the use of the lipid compounds of interest such as squalene or docosahexaenoic acid (DHA), in particular squalene, produced by means of any of the processes of the present invention, in the preparation of compositions intended for the medical field, the cosmetics field and the food sector. Thus, it relates to a method for the preparation of compositions intended for the medical field, the cosmetics field and the food sector, comprising the production of lipid compounds of interest such as squalene or docosahexaenoic acid (DHA), in particular squalene, by any of the processes of the present invention and then the preparation of compositions intended for the medical field, the cosmetics field and the food sector.

The present invention relates in particular to a product or a composition comprising the CNCM I-4469 strain or a variant thereof which retains its squalene production capacity, a biomass obtained after culturing or fermentation thereof, and a cell extract or lysate thereof. Preferably, this product or composition is a food composition or a food or nutritional supplement. It may be in liquid or solid form. In particular, it contains a lyophilisate of cells or a cell extract or lysate thereof. This product or composition may be in the form of a powder, a granule, a gel capsule, a capsule or a tablet, preferably in the form of a capsule. Alternatively, the product or composition is in liquid form and comprises the crude or refined oil obtained by means of any of the processes of the present invention.

The invention will be understood more clearly by means of the examples which follow, which are intended to be illustrative and nonlimiting.

Example 1

Study of the Production of Squalene by the *Schizochytrium* sp. CNCM I-4469 Strain In order to demonstrate the remarkable squalene production capacity of the *Schizochytrium* sp. CNCM I-4469 strain, this strain was compared with the reference microalgal strain for squalene production in the literature, namely the *Schizochytrium mangrovei* strain (RCC 893, Roscoff Culture Collection, France).

Preculture and Culture Media

The fermentation of the microalgae was carried out here in a prior preculturing phase before the actual culturing/production phase.

The preculture medium had the composition described in Table I:

TABLE I

| Preculture medium | |
|---|---|
| Glucose | 25 g |
| Yeast extracts | 2 g |
| Sodium salt of glutamic acid | 19 g |
| NaCl | 6 g |
| $MgSO_4$ | 6.5 g |
| $Na_2SO_4$ | 0.1 g |
| $CaCl_2$ | 0.1 g |
| $NaHCO_3$ | 0.1 g |
| $KH_2PO_4$ | 2 g |

TABLE I-continued

| Preculture medium | |
|---|---|
| Concentrated vitamin solution | 0.6 ml |
| Concentrated trace element solution | 0.6 ml |
| Demineralized water qs | 0.3 l |

The composition of the culture/production medium is given by Table II.

TABLE II

| Production medium | |
|---|---|
| Glucose | 75 g |
| $KH_2PO_4$ | 9.6 g |
| Yeast extracts | 12 g |
| NaCl | 2.4 g |
| Sodium salt of glutamic acid | 30 g |
| $MgSO_4$ | 12 g |
| $CaCl_2$ | 1.2 g |
| $NaHCO_3$ | 1.2 g |
| $(NH_4)_2SO_4$ | 12 g |
| KCl | 0.8 g |
| Concentrated trace element solution | 5.6 ml |
| Clearol "FBA3107" antifoam at 1 ml/l | 1 ml |
| Demineralized water qs | 1 l |

Composition of the concentrated vitamin solution in g/l:

| Vitamin B1 | 45 |
|---|---|
| Vitamin B6 | 45 |
| Vitamin B12 | 0.25 |

Composition of the concentrated trace element solution in g/l

| $MnCl_2 \cdot 2H_2O$ | 8.6 |
|---|---|
| $CoCl_2 \cdot 6H_2O$ | 0.2 |
| $NiSO_4 \cdot 6H_2O$ | 4.5 |
| $Na_2MoO_4 \cdot 2H_2O$ | 0.15 |
| $ZnSO_4 \cdot 7H_2O$ | 5.7 |
| $CuSO_4 \cdot 5H_2O$ | 6.5 |
| $FeSO_4 \cdot 7H_2O$ | 32 |

Performing the Fermentation

The preculturing was carried out in 2 l baffled Erlenmeyer flasks. The culture medium was filtered after complete dissolution of its constituents. The inoculation was carried out by taking colonies of microalgae cultured in a Petri dish (in a proportion of one 10 µl loop). The incubation lasted 48 hours, at a temperature of 25° C., with shaking at 110 rpm (on an orbital shaker).

Since the biomass settles out (or adheres to the wall), care is taken to sample 300 ml after having shaken the Erlenmeyer flasks well; said 300 ml were used to inoculate the culture.

The actual culturing was carried out in the following way in 2 l baffled Erlenmeyer flasks at a temperature of 25° C., with shaking at 110 rpm (on an orbital shaker). The initial pH was >5.5.

At equivalent glucose consumption, the culturing time was 66 h for the *Schizochytrium* sp. CNCM I-4469 strain and 138 h for the *Schizochytrium mangrovei* RCC 893 strain, reflecting better growth of the *Schizochytrium* sp. CNCM I-4469 strain.

Table III gives the results obtained with the *Schizochytrium* sp. CNCM I-4469 strain and the *Schizochytrium mangrovei* RCC 893 strain.

TABLE III

| Strain | Time (h) | Glc consumed g/l | DM g/l | % DM pellet | % squalene Crude | % squalene/DM | Squalene/l |
|---|---|---|---|---|---|---|---|
| I-4469 | 66 | 43.4 | 34.2 | 22.5 | 0.4 | 1.8 | 0.61 |
| RCC 893 | 138 | 38.2 | 20.4 | 13.5 | 0.1 | 0.4 | 0.09 |

Glc = glucose; DM = dry biomass; Squa = squalene;

Thus, it was noted that the *Schizochytrium* sp. CNCM I-4469 strain makes it possible to obtain squalene contents of 1.8 g per 100 g of dry biomass, a content never before observed with these microalgae. In comparison with the reference strain, this content is at least 4 times higher, with a culturing time which is twice as short.

Moreover, an analysis of the biomass obtained after fermentation for *Schizochytrium* sp. CNCM I-4469 made it possible to observe that it contained 41.8% by weight of total fatty acids, including 17.6% by weight of docosahexaenoic acid (DHA).

| Total fatty acids | % | 41.8 |
|---|---|---|
| Lauric acid C12:0 | % | 0.1 |
| Myristic acid C14:0 | % | 4.8 |
| Pentadecylic acid C15:0 | % | 0.4 |
| Palmitic acid C16:0 | % | 10.7 |
| Palmitoleic acid C16:1 | % | 0.2 |
| Stearic acid C18:0 | % | 0.4 |
| Oleic acid C18:1 | % | <0.1 |
| Linoleic acid LA C18:2 | % | 0.3 |
| Gamma-linolenic acid GLA C18:3 | % | <0.1 |
| Alpha-linolenic acid ALA C18:3 | % | <0.1 |
| Arachidic acid C20:0 | % | <0.1 |
| Stearidonic acid C18:4 | % | 0.1 |
| Gondoic acid C20:1 | % | <0.03 |
| Dihomo-gamma-linolenic acid C20:3 | % | 0.1 |
| Arachidonic acid AA C20:4 | % | 0.1 |
| (ETE) C20:3 | % | <0.03 |
| Behenic acid C22:0 | % | <0.1 |
| Timnodonic acid EPA C20:5 | % | 0.3 |
| Lignoceric acid C24:0 | % | <0.1 |
| Osbond acid C22:5 | % | 6.4 |
| Nervonic acid C24:1 | % | <0.1 |
| Clupanodonic acid DPA C22:5 | % | 0.2 |
| Cervonic acid DHA C22:6 | % | 17.6 |

Method for the quantification of squalene in the *Schizochytrium* sp. biomass

The analysis was carried out by proton NMR at 25° C. after bead disruption of the biomass and cold extraction with chloroform/methanol. The quantification was carried out by means of an internal standard as described below.

The spectra were obtained on an Avance III 400 spectrometer (Bruker Spectrospin), operating at 400 MHz.

Biomass disruption: Precisely weigh out approximately 200 mg of fresh biomass. Add approximately 1-1.5 cm of glass beads and 0.1 ml of methanol. Hermetically seal the tube and stir by means of a vortex mixer for at least 5 min.

Cold extraction: Add approximately 2 mg of triphenyl phosphate (TPP), 0.9 ml of methanol and 2 ml of chloroform. Hermetically seal the tube and stir by means of a vortex mixer for 1 min. Place in a refrigerator. After separation by settling out (minimum of 1 hour), carefully recover the clear upper phase and transfer it into a glass jar for evaporation to dryness, at ambient temperature, under a nitrogen stream. Dissolve the dry extract in 0.5 ml of $CDCl_3$ and 0.1 ml of $CD_3OD$ and transfer into an NMR tube.

Spectrum recording: Perform the acquisition, without solvent suppression, without rotation, with a relaxation time of at least 15 s, after having applied the appropriate settings to the instrument. The spectral window must be at least between −1 and 9 ppm with the spectrum calibrated on the chloroform peak at 7.25 ppm. Use is made of the spectrum after Fourier transformation, phase correction and subtraction of the baseline in manual mode (without exponential multiplication, LB=GB=0).

Making use of the signal: Assign the value 100 to the TPP unresolved peak not containing the chloroform signal between 7.05 and 7.15 ppm (counting as 9 TPP protons). Integrate the area of the squalene signal at 1.55 ppm (singlet counting as 6 protons).

Calculation and expression of the results: The results were expressed as crude weight percentage.

$$\text{Content} = \frac{A_s \times P_{TPP}}{6 \times 100} \times \frac{W_{TPP}}{M_{TPP}} \times M_S \times \frac{100}{PE}$$

with
$A_s$: area of the squalene signal at 1.55 ppm
$P_{TPP}$: number of protons of the integrated TPP unresolved peak: 9
$W_{TPP}$: weight, in grams, of TPP weighed out
$M_{TPP}$: molar mass, in grams per mole, of the TPP ($M_{TPP}$=326 g/mol)
$M_s$: molar mass, in grams per mole, of the squalene ($M_s$=410 g/mol)
PE: weight, in grams, of fresh biomass Example 2

Study of the Lipid Profile of the *Schizochytrium* sp. CNCM I-4469 Strain

The lipid profile of this strain (see Table IV) made it possible to determine that it also allows the production of other lipid compounds of interest, including docosahexaenoic acid (or DHA). Said profile was produced on the crude oil extracted from the biomass obtained after fermentation.

TABLE IV

Lipid profile of the strain demonstrating the compounds which are of interest

| | | |
|---|---|---|
| Lauric acid ((dodecanoic acid) 12:0) | %/com | 0.3 |
| | % surface | 0.3 |
| Tetradecanoic acid (myristic acid (14:0)) | %/com | 8.4 |
| | % surface | 10.1 |
| Pentadecylic acid C15:0 | %/com | 0.6 |
| | % surface | 0.7 |
| Hexadecanic acid (palmitic acid (16:0)) | %/com | 17.4 |
| | % surface | 20.9 |
| Hexadecenoic acid (palmitoleic acid (16:1)) | %/com | <0.3 |
| | % surface | <0.3 |
| Octodecanoic acid (stearic acid (18:0)) | %/com | 0.4 |
| | % surface | 0.5 |
| Octadecenoic acid (oleic acid (18:1 w-9)) | %/com | <0.1 |
| | % surface | |
| Octadecadienoic acid (linoleic acid (LA) (18:2 w-6)) | %/com | <0.3 |
| | % surface | <0.3 |
| Octadecatrienoic acid (alpha-linolenic acid (ALA) (18:3 w-3)) | %/com | <0.1 |
| | % surface | |
| Octadecatrienoic acid (gamma-linolenic acid (GLA) (18:3 w-6)) | %/com | <0.3 |
| | % surface | <0.3 |
| Octadecatetraenoic acid ((stearidonic acid) 18:4 w-3) | %/com | <0.3 |
| | % surface | 0.3 |

TABLE IV-continued

Lipid profile of the strain demonstrating the compounds which are of interest

| | | |
|---|---|---|
| Eicosanoic acid (arachidic acid (20:0)) | %/com | <0.1 |
| | % surface | |
| Eicosenoic acid ((gondoic acid) 20:1 w-9) | %/com | <0.1 |
| | % surface | |
| Eicosatrienoic acid ((ETE) 20:3 w-3) | %/com | <0.1 |
| | % surface | |
| Eicosatrienoic acid (dihomo-gamma-linolenic acid (20:3 w-6)) | %/com | 0.3 |
| | % surface | 0.4 |
| Arachidonic acid (ARA) (20:4 w-6) | %/com | 0.4 |
| | % surface | 0.5 |
| Eicosapentaenoic acid (EPA) (20:5 w-3) | %/com | 1.0 |
| | % surface | 1.2 |
| Docosanoic acid (behenic acid (22:0)) | %/com | <0.3 |
| | % surface | 0.3 |
| Docosapentaenoic acid ((clupanodonic acid) 22:5 (w-3) | %/com | 0.4 |
| | % surface | 0.5 |
| Docosapentaenoic acid (osbond acid (22:5 w-6)) | %/com | 12.2 |
| | % surface | 14.6 |
| Docosahexaenoic acid (DHA) (22:6 w-3) | %/com | 37.6 |
| | % surface | 45.1 |
| Tetracosanoic acid (lignoceric acid (24:0)) | %/com | <0.3 |
| | % surface | 0.3 |
| Nervonic acid ((tetracosenoic acid) 24:1 w-9) | %/com | <0.3 |
| | % surface | <0.3 |
| Squalene | % | 5.8 |
| Unidentified fatty acids | %/com | |
| | % surface | <3.9 |

Method for the Preparation of the Lipid Profile

The fatty acids were determined by gas chromatography in the form of methyl esters after transesterification with methanolic hydrochloric acid and extraction with chloroform. The results are expressed as % distribution; the analysis is carried out by the internal standardization method.

A chromatograph (Varian 3800) equipped with a split-splitless injector with a tapfocus liner and a flame ionization detector was used.

An internal calibration solution containing about precisely 0.5 mg of methyl heptadecanoate per ml of methanol was prepared. The methyl heptadecanoate served as a chromatographic point of reference.

About precisely 30 mg of pre-dried sample were weighed into a 6 ml tube. 1 ml of the internal calibration solution and then 2 ml of 3N methanolic hydrochloric acid were added using a pipette with two measurement lines. The tube was then stoppered and placed in a dry bath thermostated at 110° C. for 4 h.

After cooling, about 0.5 ml of water and 0.5 ml of saturated aqueous sodium chloride solution were added, and the extraction was carried out with 3 times 1 ml of chloroform. The chloroform phases were recovered in a 6 ml tube with them being dried on a column containing sodium sulfate. They were concentrated under a nitrogen stream to about 1 ml and injected.

The % distribution of each fatty acid (i) was obtained by the ratio of the area of the peak of this fatty acid relative to the sum of the areas of all the peaks pinpointed on the chromatogram, from lauric acid (C12:0) to DHA (C22:6 Δ4c, 7c, 10c, 13c, 16c, 19c) inclusive, with the methyl heptadecanoic peak being excluded.

The invention claimed is:

1. A method for producing a biomass comprising lipid compounds, which comprises culturing the *Schizochytrium* strain CNCM I-4469 and recovering the biomass rich in lipid compounds and, optionally, harvesting the lipid compounds therefrom, wherein the biomass comprises the lipid compound squalene and *Schizochytrium* strain CNCM I-4469 produces squalene in amounts greater than or equal to 1 g per 100 g of dry biomass produced.

2. The method according to claim 1 wherein the biomass produced further comprises the lipid compound docosahexaenoic acid (DHA).

* * * * *

SEQUENCE LISTING

<160> NUMBER OF SEQ ID NOS: 1

<210> SEQ ID NO 1
<211> LENGTH: 479
<212> TYPE: DNA
<213> ORGANISM: Schizochytrium sp

<400> SEQUENCE: 1

```
gagggtttta cattgctctc attccaatag caagacgcga agcgcccgc attgatattt      60 ctcgtcacta cctcgtggag tccacattgg gtaatttacg cgcctgctgc cttccttgga   120
tgtggtagcc gtctctcagg ctccctctcc ggagtcgagc cctaactccc cgtcacccgt   180
tatagtcacc gtaggccaat accctaccgt cgacaactga tggggcagaa actcaaacga   240
ttcatcgctc cgaaaagcga tctgctcaat tatcatgact caccaagaga gttggcttag   300
acctaataag tgcggccctc cccgaaagtc gggcccgtac agcacgtatt aattccagaa   360
ttactgcagg tatccgtata aaggaactac cgaagggatt ataactgata taatgagccg   420
ttcgcagttt cacagtataa ttcgcttata cttacacatg catggcttag tctttgaga    479
```